United States Patent
D'Ambrosio et al.

(10) Patent No.: US 8,269,176 B2
(45) Date of Patent: Sep. 18, 2012

(54) DETECTOR HEAD PROXIMITY SENSING AND COLLISION AVOIDANCE APPARATUSES AND METHODS

(75) Inventors: Raymond C. D'Ambrosio, Fremont, CA (US); Ronald J. Asjes, Valkenswaard (NL); Hugo Bertelsen, Aalborg (DK); George De Fockert, Apeldoorn (NL); Michael J. Petrillo, Pleasanton, CA (US); Alexey Korzuchin, Dublin, CA (US); Steven Rubio, San Jose, CA (US); Scott D. Heavner, Alameda, CA (US); Pierre L. Patino, Aptos, CA (US); Adrianus P. Rommers, Veldhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 528 days.

(21) Appl. No.: 12/514,593

(22) PCT Filed: Oct. 31, 2007

(86) PCT No.: PCT/US2007/083082
§ 371 (c)(1), (2), (4) Date: May 13, 2009

(87) PCT Pub. No.: WO2008/063835
PCT Pub. Date: May 29, 2008

(65) Prior Publication Data
US 2010/0061509 A1    Mar. 11, 2010

Related U.S. Application Data

(60) Provisional application No. 60/866,439, filed on Nov. 20, 2006.

(51) Int. Cl.
G21K 1/02 (2006.01)
G01T 1/20 (2006.01)
(52) U.S. Cl. .................. 250/361 R; 250/367; 250/363.1
(58) Field of Classification Search ............... 250/363.1, 250/367, 361 R
See application file for complete search history.

(56) References Cited

U.S. PATENT DOCUMENTS

| | | | |
|---|---|---|---|
| 4,593,189 A | 6/1986 | Stoub | |
| 4,942,365 A | 7/1990 | Satterwhite | |
| 4,969,170 A * | 11/1990 | Kikuchi et al. | 378/91 |

(Continued)

FOREIGN PATENT DOCUMENTS

CN    2400893 Y    11/2000
(Continued)

OTHER PUBLICATIONS

Chinese Office Action—see pp. 10 and 11.

Primary Examiner — David Porta
Assistant Examiner — Mindy Vu

(57) ABSTRACT

A gamma camera (8, 180) includes at least one radiation detector head (10, 12, 210, 212). At least one such radiation detector head (10, 12, 210, 212) includes a plurality of capacitive elements (60, 260, 76, 276) disposed over at least a radiation sensitive portion (50) of the radiation detector head. A proximity sensor monitor (62) is coupled with the plurality of capacitive elements to detect proximity of a subject to the radiation detector head based on a measured electrical characteristic of the capacitive elements. A collision sensor monitor (64) is coupled with the plurality of capacitive elements to detect conductive electric current flowing between spaced apart parallel conductive plates (66, 67) of the capacitive element responsive to mechanical deformation of the spacing between the plates.

21 Claims, 8 Drawing Sheets

U.S. PATENT DOCUMENTS

Figure 1:
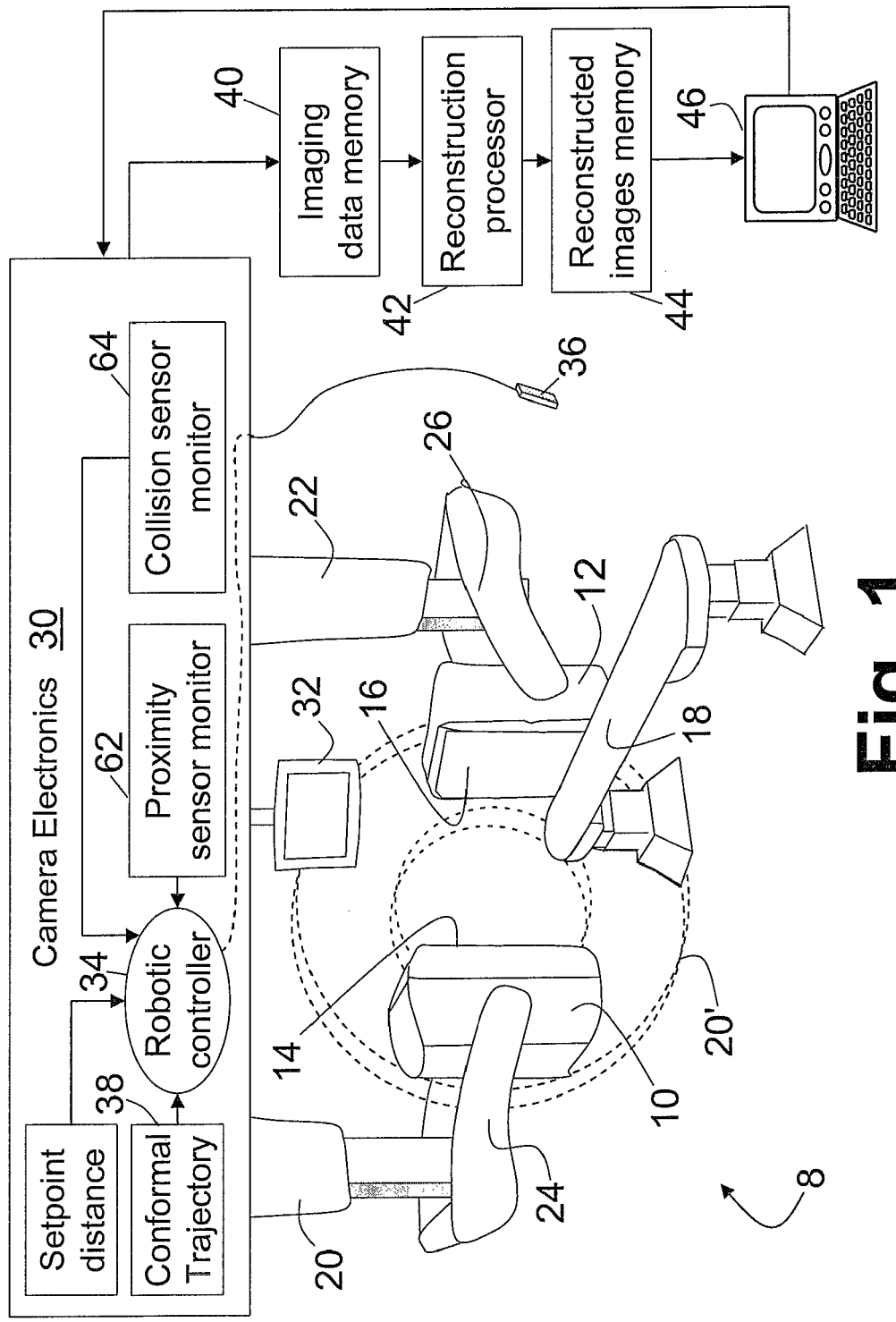

| | | | |
|---|---|---|---|
| 5,319,205 A * | 6/1994 | Kline et al. | 250/363.04 |
| 5,651,044 A | 7/1997 | Klotz, Jr. et al. | |
| 5,677,535 A | 10/1997 | Stephan | |
| 5,828,221 A | 10/1998 | Habraken et al. | |
| 6,408,051 B2 | 6/2002 | Habraken et al. | |
| 6,985,556 B2 | 1/2006 | Shanmugavel et al. | |
| 2003/0230724 A1 | 12/2003 | Koops et al. | |
| 2004/0257744 A1 | 12/2004 | Bushko et al. | |
| 2006/0097734 A1 * | 5/2006 | Roziere | 324/662 |
| 2006/0131159 A1 | 6/2006 | Kaps et al. | |

FOREIGN PATENT DOCUMENTS

| | | |
|---|---|---|
| FR | 2756048 A1 | 5/1998 |
| FR | 2896595 A1 | 7/2006 |
| WO | 2006025000 A1 | 3/2006 |

* cited by examiner

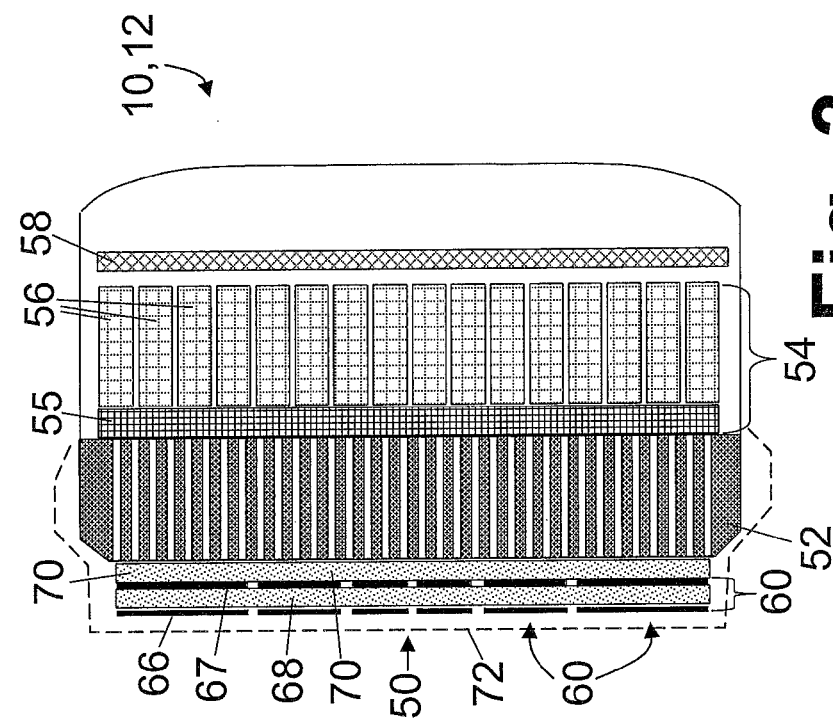
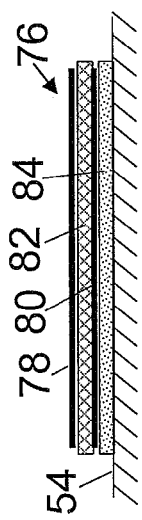
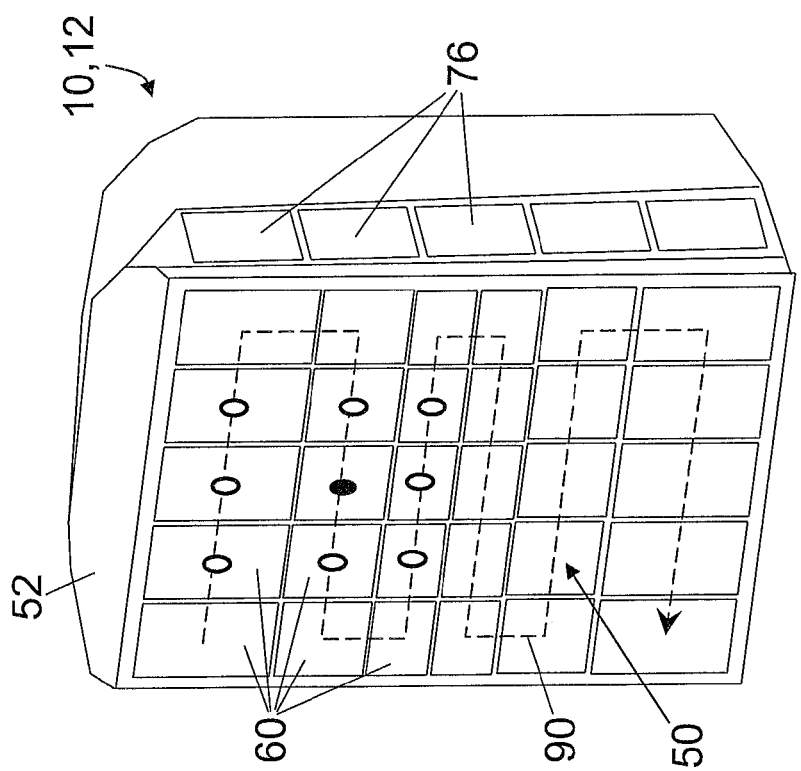
Fig. 3
Fig. 4
Fig. 2

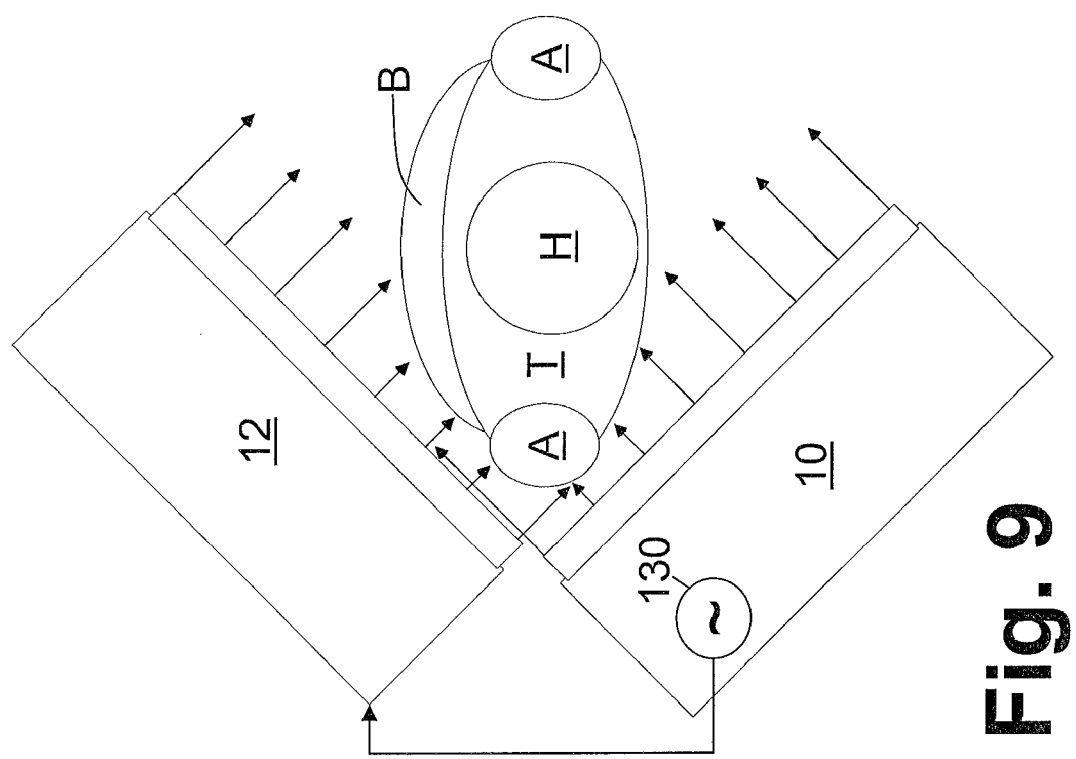

DETECTOR HEAD PROXIMITY SENSING AND COLLISION AVOIDANCE APPARATUSES AND METHODS

CROSS REFERENCE TO RELATED APPLICATIONS

This application claims the benefit of U.S. provisional application Ser. No. 60/866,439 filed Nov. 20, 2006, which is incorporated herein by reference.

The following relates to imaging, testing, diagnostic, and related arts. It finds particular application in gamma cameras, medical imaging systems including gamma cameras, tomographic medical imaging methods using gamma cameras, and so forth, and is described with particular reference thereto. However, the following finds more general application in movable detector heads of substantially any type, and in imaging systems and imaging methods employing such movable detector heads.

In nuclear medical imaging techniques such as single photon emission computed tomography (SPECT), a subject (such as a human or animal patient, a human or animal test subject, or the like) is administered a radiopharmaceutical that includes a radioisotope or other radioactive component. The radiopharmaceutical is optionally configured to aggregate in a particular tissue or organ, such as in the blood, bone tissue, liver, brain, or so forth. Because the radioisotope or other radioactive element has a certain toxicity to the subject, the dosage of the radiopharmaceutical is advantageously kept low for living subjects. The signal produced by the administered radiopharmaceutical is correspondingly low, and so radiation detector sensitivity is a substantial concern.

One technique for maximizing radiation detector sensitivity during imaging sequences is to employ a conformal tomographic trajectory in which the detector heads move toward or away from the patient during travel to maintain a small detector head-to-patient distance. However, the detector heads are relatively fragile, relatively large (in some gamma cameras, each detector head has a radiation-sensitive area of about 40 cm×50 cm), and relatively heavy (for example including a lead-based honeycomb collimator), and so collisions between the detector head and the patient are a risk.

To construct a conformal trajectory, the patient is placed onto the subject support, and the radiologist uses a hand controller to manipulate the detector head into close proximity to the patient. This close-in position (sometimes called a "mark position") is stored in a memory, and the detector head is manipulated to another close-in position providing a different angle or view of the patient to define another mark position. Several thusly defined mark positions are then interpolated to construct the conformal trajectory. This type of conformal trajectory planning must allow for a substantial detector head-to-subject gap to provide a margin of safety.

Optical proximity sensing systems are also known. These systems use a linear array of lasers or other directional light sources to define a light sheet parallel to the radiation-sensitive face of the detector head. Optical detectors arranged opposite the directional light sources detect continuity of the light sheet. When an object intersects the light sheet, the optical signal to some of the optical detectors is interrupted indicating that the light sheet has been broken. In some arrangements, two spatially offset parallel light sheets are included. If neither light sheet is broken, it is inferred that the object is too far away. If one light sheet is broken, it is inferred that an object is in the target distance range. If both light sheets are broken it is inferred that the object is too close, perhaps indicating an imminent collision.

Such optical proximity sensing systems typically project outward from the radiation sensitive face of the detector head, which can be problematic. Moreover, the provided proximity indication is discrete. In the case of a single light sheet the proximity indication is binary. For two light sheets, the proximity indication is tri-valued (zero, one, or both light sheets broken). Higher resolutions can be achieved, but at the expense of including additional light sheets. The resolution is ultimately limited by light scattering, diffraction, or other blurring effects that limit the closeness of adjacent light sheets.

In addition, the discrete proximity indications are fixed by the position or positions of the light sheet or light sheets. Adjustment of the proximity indications is either impossible, or requires adjustment of the positions of the light sheets, either manually, or through use of suitable automated optics. Such adjustment, if provided, increases the overall complexity of the optical proximity sensing system.

Further, existing optical proximity sensing systems do not distinguish the type of object breaking the light sheet. In particular, breakage of the light sheet by clothing or bedding material will be detected, so that the detector head will be positioned respective to clothing or bedding material rather than respective to the patient.

The following provides a new and improved apparatuses and methods which overcome the above-referenced problems and others.

In accordance with one aspect, a radiation detector head is disclosed, including a radiation sensitive face configured to detect radiation, and a plurality of capacitive elements disposed over the radiation-sensitive face and configured to detect proximity of a subject to the radiation sensitive face.

In accordance with another aspect, a gamma camera is disclosed, including a plurality of radiation detector heads. At least one radiation detector head includes a plurality of capacitive elements disposed over at least a radiation-sensitive portion of the radiation detector head. A proximity sensor monitor is coupled with the plurality of capacitive elements to detect proximity of a subject to the radiation detector head based on a measured electrical characteristic of the capacitive elements.

In accordance with another aspect, an imaging data acquisition method is performed using a radiation detector head including a plurality of capacitive elements disposed on a surface thereof. The imaging data acquisition method includes: moving the radiation detector head relative to a subject; acquiring radiation data from the subject using the radiation detector head during the moving or during stationary intervals between the moving; during the moving, measuring an electrical characteristic of the capacitive elements; and controlling a detector head-to-subject distance based on the measured electrical characteristic.

In accordance with another aspect, a gamma camera is disclosed, including a movable radiation detector head. At least one capacitive element is disposed on the radiation detector head and includes spaced apart parallel conductive plates. A collision sensor monitor is configured to detect conductive electric current flowing between the parallel conductive plates responsive to mechanical deformation of the spacing between the plates.

One advantage resides in providing a proximity sensor for a radiation detector head that provides a continuous, rather than discrete, indication of proximity.

Another advantage resides in providing a proximity sensor that is insensitive to pillows or clothing, so that the detector head is positioned respective to the patient in a medical application rather than respective to the patient's clothing, pillow, bedspread, or other garment or the like.

Another advantage resides in providing an electrical proximity sensor providing both continuous distance information and collision detection interlock capability.

Another advantage resides in providing a thin electrical proximity sensor having substantially no significant protrusion from the radiation-sensitive detector face.

Another advantage resides in a proximity sensor yielding continuous distance feedback combined with a scanner or controller providing a data acquisition in which the detector head-to-patient distance can be varied between patients, or between anatomical regions of the same patient, or in other ways.

Another advantage resides in providing a generally planar proximity sensor that can be constructed using well known lithographic patterning techniques.

Still further advantages of the present invention will be appreciated to those of ordinary skill in the art upon reading and understand the following detailed description.

FIG. 1 diagrammatically shows a perspective view of a gamma camera.

FIGS. 2 and 3 diagrammatically show perspective and side sectional views, respectively, of one of the radiation detector heads of the gamma camera of FIG. 1.

FIG. 4 diagrammatically shows a side sectional view of one of the capacitive elements disposed on the side of the radiation detector head as shown in FIG. 2.

Figure 5:
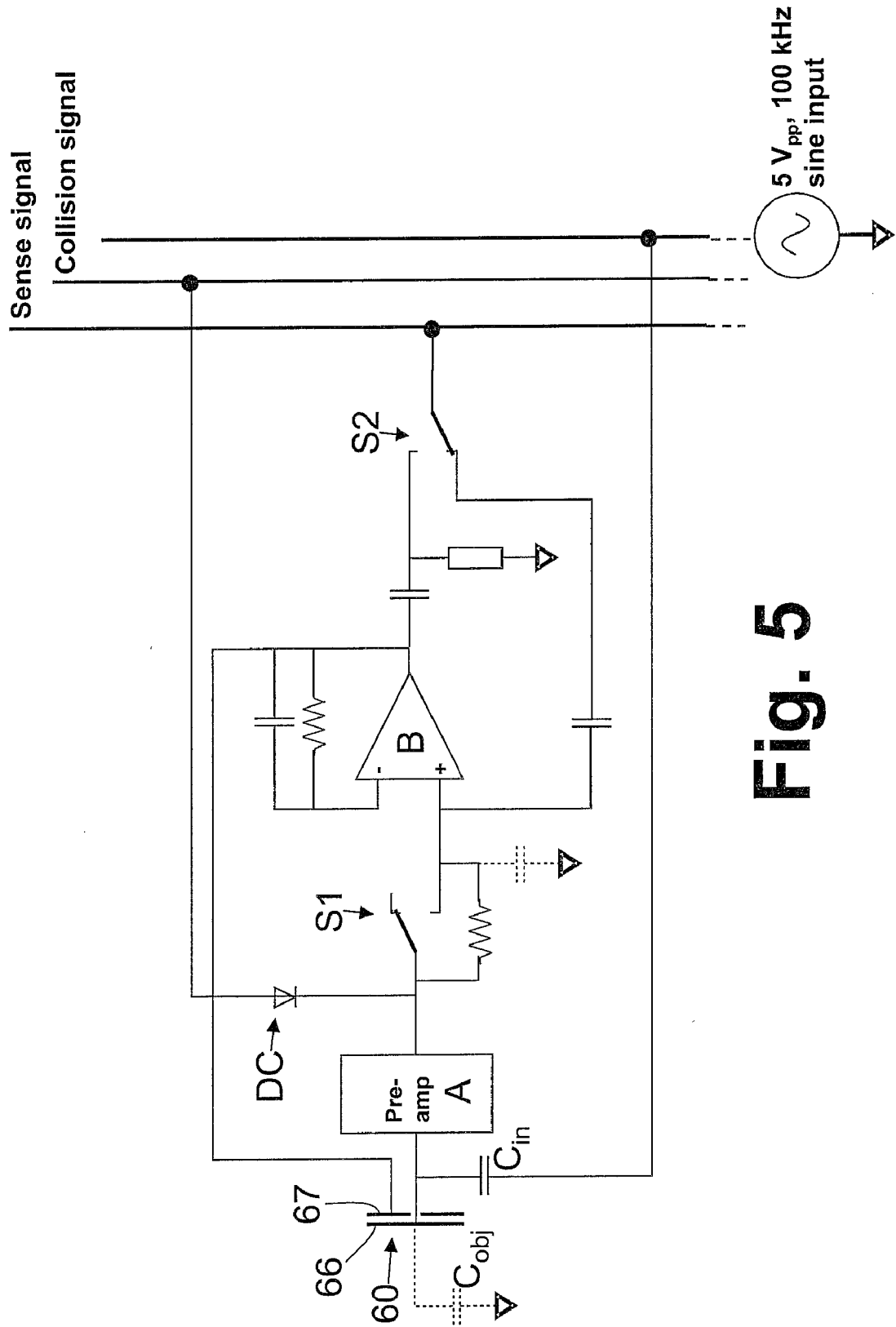

FIG. 5 diagrammatically depicts a suitable sampling circuit.

Figure 6:
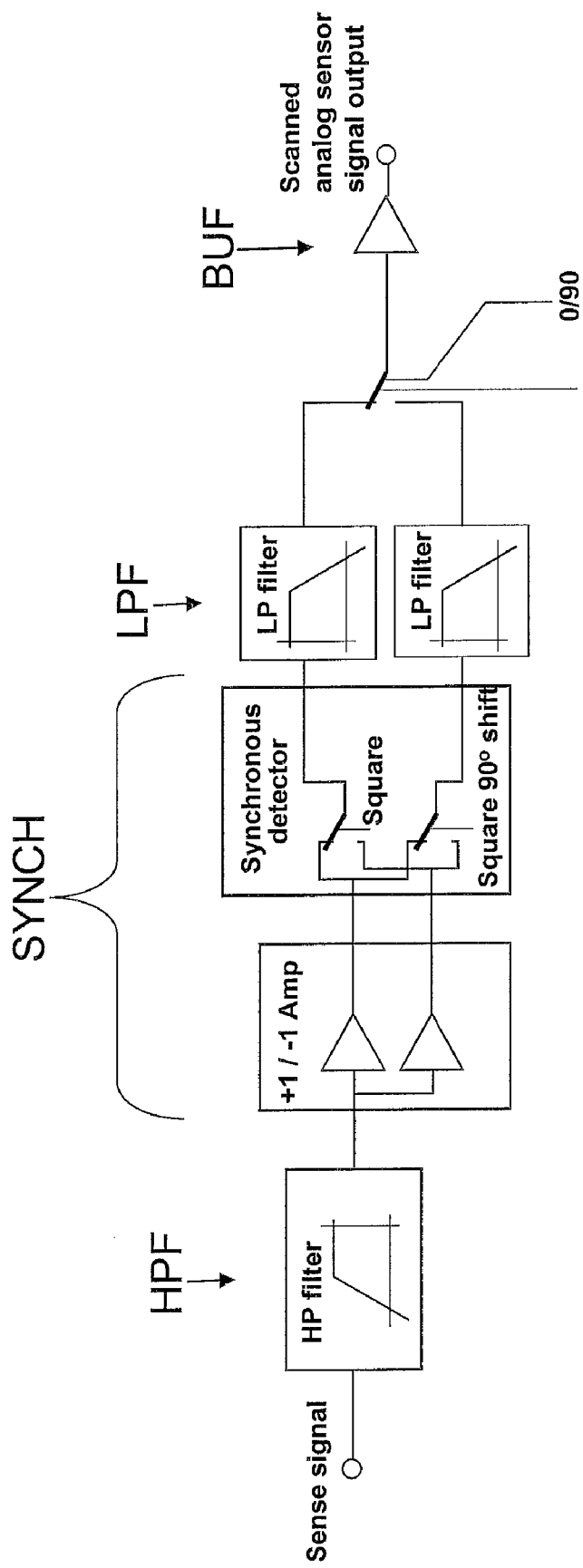

FIG. 6 diagrammatically depicts a suitable signal processing circuit for processing the sampled signal generated by the sampling circuit of FIG. 5.

Figure 7:
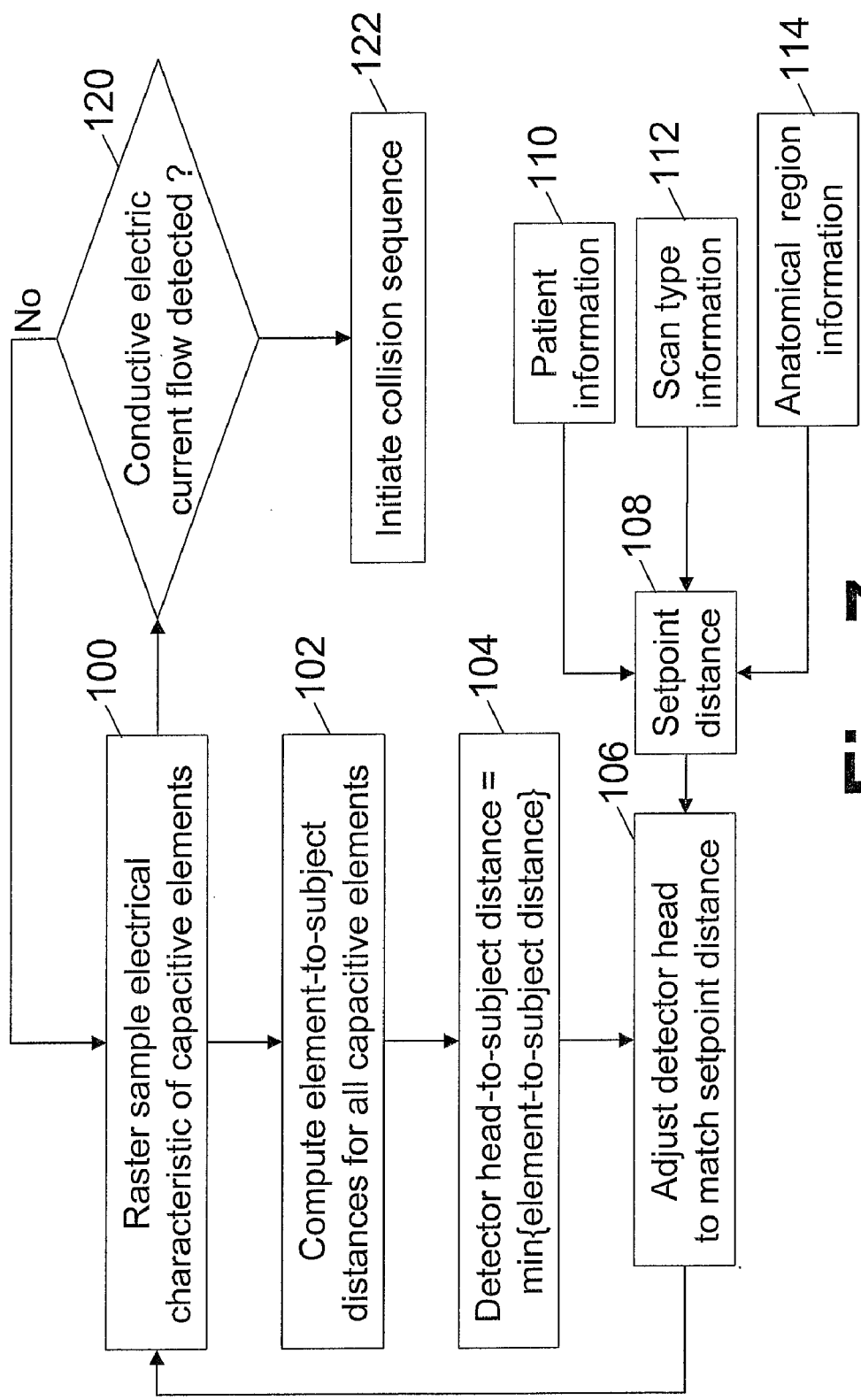

FIG. 7 diagrammatically shows a proximity control and collision avoidance method suitably performed by the system of FIGS. 1-6.

Figure 8:
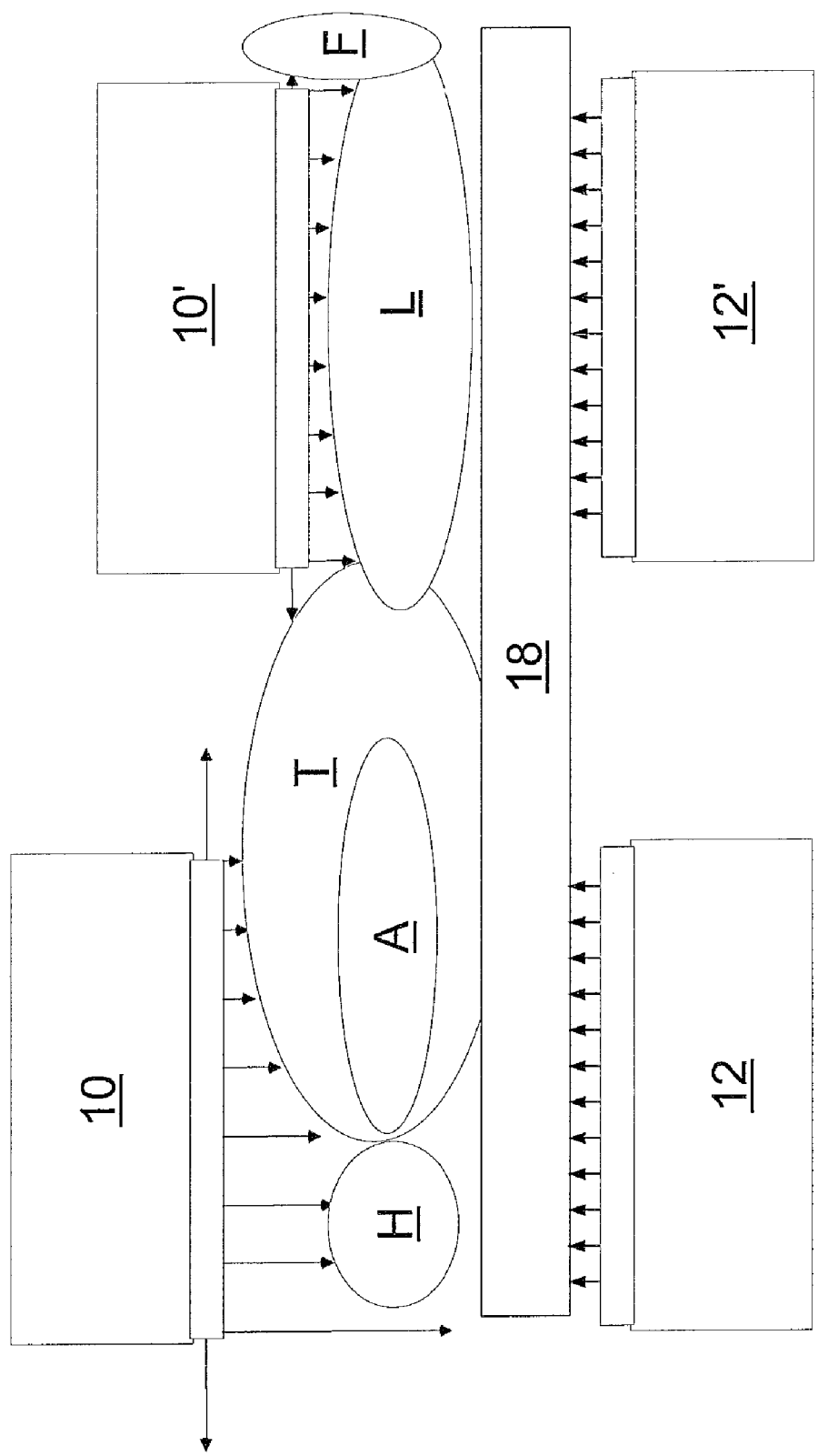

FIG. 8 diagrammatically shows proximity sensing measurements made during a total body planar imaging data acquisition.

FIG. 9 diagrammatically shows proximity sensing measurements made during a tomographic imaging data acquisition suitable for cardiac imaging.

Figure 10A:
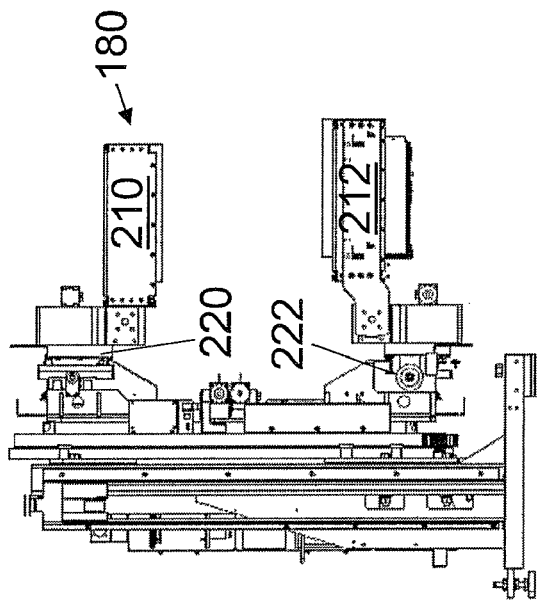
Figure 10B:
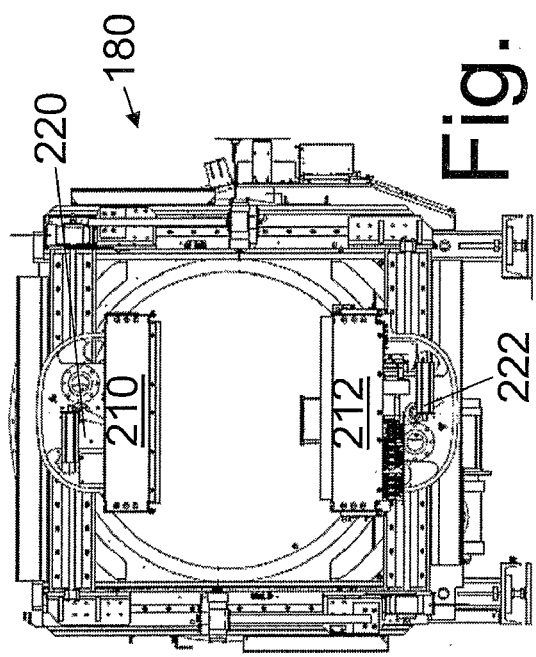
Figure 10C:
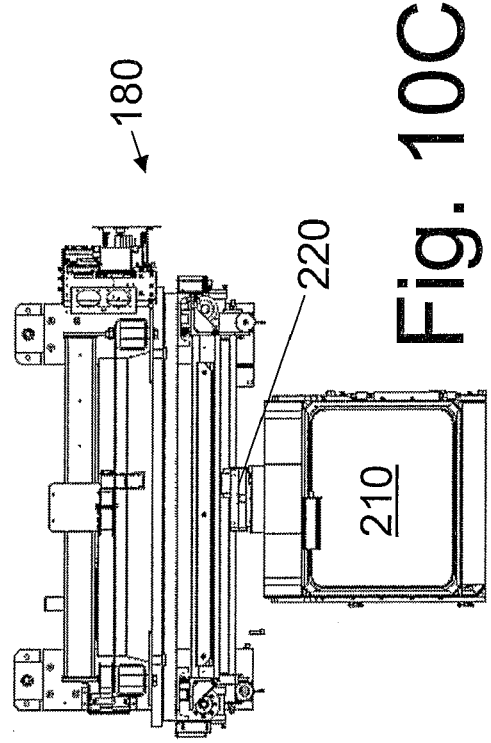

FIGS. 10A, 10B, and 10C show respective front, side, and top views of a gamma camera having a circular gantry and two radiation detector heads.

Figure 11:
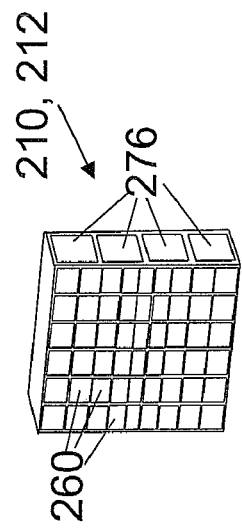

FIG. 11 diagrammatically shows a perspective view of one of the radiation detector heads of the gamma camera of FIGS. 10A, 10B, and 10C, including depiction of front- and side-mounted capacitive elements.

With reference to FIG. 1, a nuclear medical imaging system includes a gamma camera 8, which in the illustrated embodiment includes two radiation detector heads 10, 12. In other embodiments, the gamma camera may include one, two, three, four, five, six, seven, or more detector heads. The radiation detector heads 10, 12 have respective radiation-sensitive faces 14, 16, which are generally arranged to face a patient support or pallet 18. The illustrated detector heads 10, 12 are supported by respective articulated, multi-jointed robotic arms 20, 22. Each robotic arm 20, 22 includes a combination of electronically controllable translational, rotational, swivel, or other mechanical joints that cooperatively or collectively enable several degrees of movement freedom, such as radial movement of the detector heads 10, 12 toward or away from the patient couch 18, tangential movement of the heads in a direction transverse to the radial movement, circumferential movement, or so forth. Each of the illustrated robotic arms 20, 22 terminates in a forked support member 24, 26, respectively. The forked support members 24, 26 directly support the detector heads 10, 12, respectively.

Camera electronics 30 provide control of the articulated robotic arms 20, 22, deliver power to the robotic arms 20, 22 and the detector heads 10, 12, and output radiation detection information from the detector heads 10, 12. The camera electronics 30 are optionally coupled with a video monitor 32 for displaying various information about the status and operation of the gamma camera 8.

The illustrated gamma camera 8 including the radiation detectors 10, 12, patient support 18, robotic arms 20, 22, camera electronics 30, and video display 32 is suitably embodied by the Skylight™ nuclear camera (available from Philips Medical Systems, Eindhoven, The Netherlands). However, the detector head distance sensing and collision avoidance apparatuses and methods disclosed herein can be practiced with substantially any type of gamma camera that provides one or more radiation detectors capable of conformally moving around or about a patient. For example, it can be used in conjunction with gamma cameras having a larger number of smaller detector heads. In some embodiments, the robotic arms 20, 22 are replaced by a ring gantry 20' (drawn in phantom in FIG. 1) that supports the detector heads 10, 12. In these embodiments, the ring gantry 20' includes a rotatable gantry portion supporting the heads 10, 12 so as to enable revolving of the heads 10, 12 around the couch 18, and gamma detector head mounting fixtures (not shown) that provide radial and tangential movement of the detector heads. In either a ring gantry or robotic arm mounting arrangement, the terminating mount structure that directly connects with the radiation detector heads can be other than the illustrated forked support members 24, 26. For example, the forked support members 24, 26 could be replaced by a single sided mounting arm positioned at the side or rear of the detector head, an asymmetric arrangement including several mounting posts, or so forth. The gamma camera 8 can also include other features that are, for brevity, not illustrated in FIG. 1, such as an automated collimator exchanger which is available for the Skylight™ nuclear camera and some other gamma cameras.

With continuing reference to FIG. 1, the camera electronics 30 include a robotic controller 34 that is operable by a hand controller 36 in a manual mode to manipulate the detector heads 10, 12 using the robotic arms 20, 22. Alternatively, the robotic controller 34 can be operated using a suitable control algorithm implemented by the camera electronics 30 to move the detector heads 10, 12 along a predetermined conformal trajectory 38. In some embodiments, the video monitor 32 can be configured to output in a persistent "p scope" mode which displays a map of radiation detections corresponding to the detector face of a selected one of the detectors 10, 12. A radiologist or other operator suitably uses the hand controller 36 in conjunction with the "p scope" display, visual observation of the position of the detector head, or other feedback to determine several close-in detector head positions, i.e., mark positions, from which a conformal trajectory 38 may be interpolated or otherwise constructed.

To acquire tomographic imaging data, the robotic controller 34 manipulates the detector heads 10, 12 using the robotic arms 20, 22 to move the detector heads 10, 12 substantially in accordance with the conformal trajectory 38. During this automated trajectory traversal, the detector heads 10, 12 collect imaging data that is stored in an imaging data memory 40. For example, the imaging data may be projection data in the case of SPECT imaging, or line-of-response data if the gamma camera is being used in a PET imaging mode, or so forth. A reconstruction processor 42 applies a suitable reconstruction algorithm, such as a filtered backprojection reconstruction algorithm, an iterative reconstruction algorithm, or so forth, to compute a reconstructed image from the collected imaging data. The reconstructed image is stored in an images memory 44, and may be displayed on the display of a user interface 46, or stored for later retrieval in an electronic, magnetic, or optical memory, or transmitted via a local area network or the Internet, or processed by post-reconstruction image processing, or otherwise utilized. In the illustrated embodiment, the user interface 46 also provides user interfacing with the camera electronics 30. In other embodiments, the video monitor 32, hand controller 36, or another user interfacing device may be used instead of or in addition to the user interface 46 to provide user interfacing with the camera electronics 30.

With continuing reference to FIG. 1 and with further reference to FIGS. 2 and 3, each detector head 10, 12 includes a generally planar radiation-sensitive face 50 that in the illustrated embodiment includes a collimator 52. The collimator 52 is a pinhole, honeycomb, or other type of collimator made of radiation absorbing material and having pinholes, openings, or filled radiation transmissive regions that collimate incoming radiation in a direction generally transverse to the generally planar radiation-sensitive face 50. In other embodiments, a slat-type collimator may be used that collimates incoming radiation into planes. In yet other embodiments, the collimator may be omitted, for example if the detector head is being used for positron emission tomography (PET) imaging. The illustrated detector heads 10, 12 each further include an array of radiation detectors 54. The illustrated radiation detectors 54 include one or more scintillators 55 optically coupled with a plurality of photomultiplier tubes 56 arranged to view the one or more scintillators 55. The photomultiplier tubes 56 are optionally replaced by another type of light sensor, such as an array of photodiodes. The term "light" as used to denote scintillation output of the one or more scintillators 55 encompasses both visible light and invisible ultraviolet or infrared light. The outputs of the photomultiplier tubes 56 are input to electronics, for example disposed on a printed circuit board 58. Instead of the scintillator-based radiation detectors 54, a plurality of radiation sensitive elements, such as, for example, solid state CZT based detectors, can be used to directly absorb radiation and output an electrical signal responsive thereto.

With continuing reference to FIG. 1 and with further reference to FIGS. 2-4, one or both of the detector heads 10, 12 further include a proximity or distance sensing system including a plurality of capacitive elements 60 (FIGS. 2, 3, and 4), a proximity sensor monitor 62 (FIG. 1), and a collision sensor monitor 64 (FIG. 1). The illustrated capacitive elements 60 are planar capacitors, such as parallel plate capacitors each including (as seen in FIG. 3) first and second parallel conductive plates 66, 67 spaced apart by air or an insulative material 68, such as a foam material, dielectric material, epoxy, or so forth. If the capacitive elements are to be used in the conductive collision-sensing modality described herein, then the insulative material 68 should be arranged as spaced apart spacer elements with substantial air gaps in-between such that the plates 66, 67 can be compressively brought into contact with each other, or at least close enough to enable flow of conductive current across the mechanically compressed spacer. Thus, in some embodiments, the spacer is a grid, array, or other configuration of foam, dielectric material, or so forth having substantial areas of separation between the spacers between which the parallel plates can be compressively brought together to implement collision sensing. On the other hand, if the capacitive elements are used only in a capacitive sensing mode without electrically conductive collision sensing, then the conductive plates 66, 67 can be spaced apart by a more rigid dielectric material that optionally substantially fills the space between the conductive plates 66, 67. Moreover, instead of parallel plate planar capacitors, other configurations can be used, such as a planar sense capacitor and a non-planar second conductive element. It is also contemplated to employ the collimator 52 as the second conductor of the capacitor, although if the collimator is electrically grounded then it cannot be used as a conductive plate of the capacitive element. In the illustrated embodiment, the planar capacitors 60 are parallel plate capacitors having two conductive plates 66, 67, with the bottom or lower plate 67 spaced apart from the collimator 52 by an insulative material 70, such as a foam or other dielectric layer. In some embodiments, the insulative material 70 is arranged as a grid or array of spacer elements with air gaps in-between. In a suitable manufacturing approach, the parallel conductive plates 66, 67 are each a conductive film, such as a copper film, disposed on a generally planar dielectric substrate defining the insulative layer 68, in which the conductive film is patterned to define the array of parallel-plate capacitors 60 and optionally also electrical interconnect traces. In the illustrated embodiment, the conductive films 66, 67 are patterned in the same way such that each parallel plate capacitor has substantially equally sized conductive parallel plates 66, 67. In other contemplated embodiments, the two conductive films may be patterned differently to give parallel plates of different areas. The capacitive elements 60 are disposed over the radiation-sensitive face 50, optionally, within an outer cover 72 of the radiation-sensitive face 50 (optional outer cover diagrammatically indicated by dashed lines in FIG. 3). The conductive parallel plates 66, 67, insulative materials or layers 68, 70, or other elements of the capacitive elements 60 should be selected to avoid substantially attenuating the radiation that is detected by the scintillator 55.

Additional capacitive elements 76 are additionally or alternatively disposed on one or more sides of the radiation detector head 10, 12 to detect side proximity. With particular reference to FIG. 4, in the illustrated embodiment the side-mounted capacitive elements 76 are parallel plate capacitors formed by patterning of copper layers 78, 80 laminated on opposite sides of an epoxy board 82 of a double-sided printed circuit board that is spaced apart from the side of the collimator 54 by a foam layer 84. Because radiation is not detected through the side-mounted capacitive elements 76, these elements are optionally made of a radiation absorbing material. In this approach, the epoxy board 82 of the printed circuit board defines the insulative layer spacing apart the parallel conductive plates 78, 80.

With continuing reference to FIGS. 1-4, the proximity sensor monitor 62 suitably measures an electrical characteristic of each capacitive element 60, 76, such as a capacitance, an impedance, or an admittance. Proximity of an electrically conductive body, such as a human body, a fluid containing or carrying intravenous bag or tube, or so forth, will induce a change in the capacitance of the proximate capacitive element by an amount dependent upon the closeness or quantitative proximity of the conductive body. Thus, the value of the capacitance or other measured electrical characteristic will change as a patient or other conductive body moves toward or away from the capacitive element. On the other hand, bedding material or clothing is not electrically conductive, and hence induces little or no change in the capacitance even at very close proximity.

In a suitable measuring approach, the proximity sensor monitor 62 applies an a.c. electrical signal or a.c. electrical signal component to a specific parallel plate capacitor of the plurality of capacitive elements 60, 76, and detects the measured electrical characteristic generated responsive thereto. In FIG. 2, for example, a back-and-forth raster sampling of the capacitive elements 60 is indicated by a rastering path shown by dashed line 90. A currently sampled capacitive element is denoted by a filled circle marker in FIG. 2. The proximity sensor monitor 62 applies the a.c. electrical signal or a.c. electrical signal component to the capacitive element denoted by the filled circle, and measures a responsive signal for example using a synchronous or coherent measurement technique such as is discussed for example in Satterwhite, U.S. Pat. No. 4,942,365, which is incorporated by reference herein in its entirety. An impedance or admittance of the capacitive element can be determined, for example based on a ratio of the output signal phasor and the input signal phasor. The capacitance is optionally determined from the impedance or admittance, or the impedance or admittance may be directly used as the measured electrical characteristic.

In some embodiments, the proximity sensor monitor 62 is further configured to bias neighboring capacitive elements (indicated in FIG. 2 by open circle markers) to reduce an effect of the neighboring capacitive elements on the measured electrical characteristic of the sampled capacitive element (indicated in FIG. 2 by the filled circle marker). In an iterative approach, an initial measurement of the sampled capacitive element is acquired to determine its voltage. The neighboring capacitive elements are then actively driven to that voltage and another measurement of the sampled capacitive element is acquired. The process is optionally repeated to further refine the measurement of the sampled capacitive element.

The relationship between the measured electrical characteristic and the detector head-to-patient distance is suitably determined empirically as follows. An initial value for the measured electrical characteristic is sampled without the subject in the vicinity, to establish an "infinite distance" calibration point. Additional samples are acquired at different detector head-to-patient distances to develop a calibration curve. Additionally or alternatively, the relationship between the measured electrical characteristic and the detector head-to-patient distance can be determined by first principles electrostatic calculations. By raster sampling the capacitive elements 60 using the raster path 90 or another suitable sampling pattern, all the capacitive elements 60 can be sampled in a selected time interval, such as every second or every tenth second. The proximity is suitably defined as the smallest proximity indicated by any of the sampled capacitive elements 60. Moreover, in some embodiments a proximity map is computed in which each proximity map element is the proximity measured by a corresponding capacitive element. Such a proximity map can be used to recognize, for example, when the detector head is moving in a direction taking it away from the patient (so that the robotic arm should begin to move the detector head toward the patient) versus when the detector head is moving in a direction taking it toward the patient (so that the robotic arm should begin to move the detector head away from the patient).

The accuracy of the proximity measurement is typically inversely proportional to an area of the parallel plate capacitor 60, 76. On the other hand, smaller plate areas provide higher spatial resolution. In the illustrated embodiment shown in FIGS. 2 and 3, the parallel plate capacitors 60 are of varying size, with the largest-area plates near opposing edges of the radiation sensitive face 50 and the smallest plates near a center of the radiation sensitive face 50. This arrangement is selected based on cost and space considerations. More capacitive elements increases the cost of the pre-amplification or other operating circuitry because the number of electronic components and circuit board area coverage typically scales linearly with the number of capacitive elements used for sensing. However, other arrangements can be selected. For example, in some contemplated embodiments, parallel plate capacitive elements of all equal size are used.

An advantage of the capacitive proximity sensing is that it is substantially insensitive to non-conductive materials such as bedding or clothing materials. However, this advantage can be disadvantageous in the event that a relatively rigid non-conductive body actually impacts the detector head.

With continuing reference to FIGS. 1-4, the collision sensor monitor 64 addresses this concern by using conductive current flow information from the parallel plate capacitors 60, 76. In some embodiments incorporating the collision sensor monitor 64, the insulative layer 68 is made of a deformable or compliant material that can be compressively deformed to bring the plates 66, 67 into contact, or at least sufficiently close together to allow for flow of conductive electrical current between the plates. Under suitable bias from the collision sensor monitor 64, a conductive electric current will therefore flow between the parallel conductive plates 66, 67 responsive to compressive deformation of the compliant material 68 that allows the parallel conductive plates 66, 67 to contact each other or come into sufficiently close proximity to each other to produce an electrically conductive shunt. Thus, the parallel plate capacitors 60 and the collision sensor monitor 64 define a binary switch that detects a collision. Unlike proximity detection, the collision detection relies upon mechanical deformation of the compliant insulative layer, and hence collision is detected regardless of whether the colliding body is electrically conductive or electrically insulating.

In FIG. 1, the proximity sensor monitor 62 and the collision sensor monitor 64 are shown as separate components. In some embodiments, these two components may be partially or wholly integrated together. For example, a unitary sensor monitor may apply a signal to a presently sensed capacitor that includes a d.c. bias and a superimposed a.c. bias. The d.c. bias component is used to monitor for conductive current flow indicative of collision, while the a.c. bias component is used for proximity sensing. Alternatively, only an a.c. component may be used, and the complex impedance or admittance measured. The real component of the complex impedance or admittance is indicative of conductive current flow, while the imaginary component of the complex impedance or admittance is suitably used for the proximity sensing.

With reference to FIG. 5, a diagrammatic electrical schematic sampling circuit is shown that is suitable for sampling the capacitive elements 60. Switches S1, S2 are mainly used to perform the raster scanning. Only one of the front sensor plates 66 is connected to the sense signal at a time, while the front sensor plates 66 of the other capacitive elements 60 of the array are forced to the same potential as the measuring sensor plate 66. This reduces the likelihood of measurement distortion being caused by neighboring capacitive elements affecting the field lines. The collision detection is independent of how the switches S1, S2 are set. Rather, any time any of the plates 66, 67 of any of the capacitive elements 60 come into contact with each other, a conductive electrical current flows through the diode DC and the line labeled "Collision signal" and this conductive current flow is interpreted as an indication of a collision.

With continuing reference to FIG. 5, the proximity sensing operates as follows. A 100 KHz sine oscillator ($5V_{pp}$) is connected with the front plate 66, also called the sensor or sensing plate, being measured via the sense signal line. This connection causes the front sensor plate 66 to emit an electric field which propagates through the optional protective cover 72 and the air towards any nearby object at a different potential. The electric field is biased in the direction of the object by feeding the sensor input signal back to the guarding element capacitive plate 67 behind the front sensing plate 66 via a unity gain amplifier B and to the neighboring guarding elements via the settings of the switches S1, S2 as illustrated in FIG. 5. Because of a strong capacitive coupling the neighboring front sensor plates 66 are also kept at the guarding signal level preventing field lines going from the measured sensing plate 66 to neighboring front plates 66. A preamplifier A connected with the measured sensing plate 66 has a high input impedance, which causes the input voltage to this amplifier to be approximately a voltage division between an input capacitance $C_{in}$ and the capacitance of the object in front of the sensing plate 66, denoted $C_{obj}$ herein. The input capacitance $C_{in}$ is chosen to be approximately equal to the capacitance the sensing element 66 sees with no proximate object. In some embodiments, $C_{in}$ is set to about 1.5 pF, although other values can be used. The result is a 2.5 $V_{pp}$ signal at the input of preamplifier A when there is no proximate object. As an object is approaching proximity to the sensing plate 66, the capacitance of the proximate object increases, which results in a lower input signal at preamplifier A. The lowest signal at the input of preamplifier A of a few hundred mV is achieved by putting a large grounded object in close proximity to the sensing plate 66, for example close to contacting the optional protective cover 72.

Not shown in FIG. 5 is a first order high-pass filter at the input stage of each preamplifier A that blocks 50 Hz or 60 Hz noise from electrical equipment from saturating the amplifiers. In some embodiments, the 3 dB cutoff frequency for this filter is approximately 3 kHz.

The system is robust against failure of one or a few capacitive elements 60. For example, if a wire to a sense element 66 is broken, then the voltage division between $C_{Obj}$ and $C_{in}$ will not take place and the input amplifier A will see the full $5V_{pp}$ signal. This is above the normal operating range of any proximate object, so the proximity sensor monitor 62 suitably generates an error message or otherwise handles the erroneous reading. If a wire to a guard element 67 is broken, then the guard signal will follow the potential of the collimator 52 behind the guard sensor 67, which in this embodiment is grounded. This will result in an input signal to the preamplifier A that is below the normal operating range of any proximate object. In this case the proximity sensor monitor 62 suitably generates an error message or otherwise handles the erroneous reading. During a collision the sense and guard plates 66, 67 of a capacitive element 60 are shorted. Because the guard 67 is connected to −5V from a DC perspective, this allows conductive electrical current to run through the diode DC, and then drive the collision signal. FIG. 5 does not show the additional circuitry for handling this conductive electrical current, but a comparator and open-collector circuitry is suitably used.

With reference to FIG. 6, the synchronous detector, or the analog-to-digital converter, and microprocessor containing firmware for computing the distance and compensating for gain and offset errors is described. The circuit of FIG. 6 receives the "Sense signal" and performs high pass filtering using a high-pass ("HP") filter HPF, synchronous demodulation using a synchronous demodulation block SYNCH and a square-wave input at 0° and 90° phases, low pass ("LP") filtering of the demodulated signal using low-pass filters LPF, and optional further signal processing such as analog-to-digital conversion, root mean square (RMS) or other averaging calculation, gain correction, offset correction, or the like (diagrammatically indicated by a buffer BUF in FIG. 6). The output of the buffer BUF is suitably used by the proximity sensor monitor 62 in determining proximity.

In an actual reduction to practice, a radiation detector head was built that included a 6×9 array of fifty-four parallel plate capacitors spanning the area of the radiation-sensitive face. The area of these capacitors was varied similarly to as shown in FIGS. 2 and 3, between a largest area capacitor of 9×9 $cm^2$ and a smallest area capacitor of 9×3 $cm^2$. The capacitors were formed of seventeen-micron-thick patterned copper sheets spaced apart by 5 mm wide, 1.6 mm high foam strips distributed across the cover surface at approximately 10 cm apart. Accordingly, the space between the copper sheets was mostly air, which is advantageous for the collision-sensing application in which the two sheets are mechanically compressed together to generate a conductive electrical current signal. A similar arrangement of foam strips spaced 10 cm apart was used to separate the bottommost conductive layer from the collimator. A plastic outer covering was placed over the array of capacitors disposed over the radiation-sensitive face. The electronics were configured to perform a round of raster sampling of the 54 capacitive elements in about 1 millisecond, enabling the entire detector to measure the distance to the object about 16 times per second. In the actual reduction to practice, the side capacitive elements were made by patterning the conductive layers of a double-sided printed circuit board. Side collision detection was provided by monitoring for conductive electric current flow between a track on the backside of the printed circuit board to ground via an L-bracket connected to the collimator frame.

The illustrated embodiments include both proximity sensing and collision detection capabilities. However, it is contemplated to include only one or the other of these capabilities in a given embodiment. For example, the detector head may omit the proximity sensing capability but include the collision detection aspect so as to provide a safety interlock protecting against discomfiting or injuring the patient or damaging the detector head. Conversely, the detector head may include the proximity sensing capability but omit the collision detection capability. In this latter embodiment, collision protection respective to conductive bodies may be provided by interlocking the robotic controller 34 against moving the detector heads 10, 12 closer than a selected minimum detector head-to-subject distance.

The illustrated capacitive elements 60, 76 are planar capacitors having conductive plates 66 distributed across and aligned parallel with the radiation-sensitive face. This provides a low profile proximity detector that extends only a short distance away from the radiation-sensitive face 50. For example, the embodiment that was reduced to practice included parallel-plate capacitors with a thickness of 1.6 millimeter (for the thick foam layer) plus twice the seventeen micron (0.017 millimeter) thickness of the patterned copper sheets, for a total thickness of less than 2 millimeters. More generally, the capacitive elements optionally extend less than 5 millimeters from the radiation-sensitive face 50, so that the proximity detector does not itself introduce undesired additional separation between the radiation-sensitive face 50 and the subject.

The capacitive proximity sensing system is suitably used to simplify the workflow of SPECT imaging data acquisition. In one approach for tomographic imaging, the radiologist or other operator selects the desired start angle and detector orientation, and commands the system to start the study. The robotic manipulators 20, 22 automatically move the detector heads 10, 12 to the desired initial azimuth angle, and slowly decrease their radius until the desired detector-to-patient separation is detected using the capacitive proximity sensing. At the end of imaging data acquisition at each azimuth, the robotic manipulators 20, 22 move the detector heads 10, 12 a small distance away from the patient in order to reorient the detector heads 10, 12 for the next azimuth. The capacitive proximity sensing is again used to locate the patient, and decrease the spacing to the desired distance. This is repeated for each azimuth angle. Since the distance measurement is continuous, the operator may choose the desired distance, and may also elect to increase or decrease this distance during the course of the study.

The side-mounted capacitive elements 76 are installed on the leading and trailing edges of the detector heads 10, 12. These are suitably used, for example, for total body planar imaging applications. In such studies, the detector heads 10, 12 are oriented above and below a reclining patient, and move along the patient's body from head to toe (or toe to head). As the detector heads 10, 12 move along the patient's body, they are suitably raised or lowered to avoid contact with anatomy of varying height, such as breasts, abdomen, feet, or so forth. In such a planar scan application, the side-mounted capacitive elements 76 measure the distance ahead of the detector along the body axis, to allow sufficient time to raise the detector head to avoid tall objects. In some embodiments, the operator workflow is as follows: the start and stop distances are selected to indicate the overall scan length, and the gamma camera 8 is commanded to begin acquiring imaging data. The capacitive proximity sensing is used to automatically determine each detector head relative angle and table start position, decreases the detector radius to the desired distance from the patient, and then begins acquiring.

Even in static imaging data acquisition scenarios, where automatically controlled detector orientation is not relevant, the capacitive proximity sensing is helpful to the operator. Since the side-mounted capacitive elements 76 can detect objects ahead of the detector head, they can be used during hand-controller operation of the robotic manipulators 20, 22 to position the heads 10, 12. When proximity to the subject is detected, the head movement is suitably slowed down and stopped before making contact with the subject. The collision sensing capability can be used as a secondary fail-safe during such hand-controller operated detector head positioning.

With reference to FIG. 7, a suitable proximity control and collision avoidance method performed by the monitors 62, 64 in conjunction with the capacitive elements 60, 76 is described. In a rastering operation 100, the proximity sensor monitor 62 successively samples the capacitive elements 60, 76, for example using the raster path 90 (shown in FIG. 2) or another suitable sampling pattern. The rastering operation 100 measures an electrical characteristic of each sampled capacitive element, such as a measured capacitance, admittance, impedance, or so forth. In a computation 102, an element-to-subject distance is computed for each capacitive element based on its measured electrical characteristic. A computation 104 determines a detector head-to-subject distance from the individual element-to-subject distances. In the embodiment of FIG. 7, the computation 104 takes the minimum element-to-subject distance as the detector head-to-subject distance. This approach reduces the likelihood of overestimating the detector head-to-subject distance which can be advantageous for safety. However, the computation 104 can use other formulations, such as taking an average of the smallest N element-to-subject distances where N is an integer selected to provide some robustness against an occasional erroneous element-to-subject distance measurement or malfunctioning or failed capacitive element. Similarly, the computation 104 may incorporate filtering outlier values. An outlier value may be identified, for example, as a measured element-to-subject distance that is very different from the element-to-subject distances measured for neighboring capacitive elements.

With continuing reference to FIG. 7, a control operation 106 operates the appropriate robotic arm 20, 22 to adjust the positioning of the detector head 10, 12 to match a setpoint distance 108. The setpoint distance 108 can be generated in various ways. In some embodiments, the setpoint distance 108 is a constant distance selected based on the mechanical tolerances of the gamma camera 8 and the desire to keep the detector head-to-subject distance small during imaging. Other factors may optionally be incorporated into the setpoint distance 108, such as considerations regarding the patient (for example, if patient information 110 indicates that the patient is claustrophobic, then a larger setpoint distance 108 may be selected). Another factor that may optionally be incorporated is scan type information 112. For example, if the scan is one that uses a low signal-strength (or low dosage) radioisotope, a smaller setpoint distance 108 may be selected compared with a scan that uses a higher signal-strength (or higher dosage) radioisotope. The scan type information 112 may also be used in selecting the setpoint distance 108 to reflect a tradeoff between patient comfort and the need for high resolution or good image quality for the scan type being performed. If the scan type is a two-part (or more-part) study, for example using two different isotopes at different times during the study, then the setpoint distance 108 may be changed over time during the study to, for example, move the detector heads closer when using a lower-signal isotope. For a tomographic scan, the setpoint distance 108 may be adjusted based on angular or azimuthal position, for example to move the detector relatively closer when the region of interest is further away from the radiation detector head.

As yet another illustrative factor, anatomical region information 114 may be taken into account, with the setpoint distance 108 being changed for imaging of different anatomical regions, even within the same imaging scan. For example, in a head-to-toe body scan, the setpoint 108 may be set lower (that is, smaller detector head-to-subject distance) when imaging the torso region which is relatively large and contains critical anatomical features, as compared with imaging the head region which is relatively smaller. A relatively larger detector head-to-subject distance may also be appropriate for the head region since this imaging places the detector head in front of the patient's face, which can be uncomfortable for the patient. The factors 110, 112, 114 are illustrative examples, and additional or other factors such as the radiologist's personal preference, governing regulatory or best medical practice rules, or so forth may also be taken into account in determining the setpoint 108.

With continuing reference to FIG. 7, the collision avoidance system is also advantageously operative during imaging. During the rastering operation 100, as each capacitive element is sampled a check 120 is made as to whether conductive electrical current flow is detected. If such conductive current flow is detected by the collision sensor monitor 64 (see FIG. 1), then a suitable collision sequence 122 is initiated. The collision sequence may involve, for example, setting off an audible and/or visual alarm, stopping all movement of the detector heads 10, 12 or withdrawing the detector heads 10, 12 to a safe position away from the patient, or so forth.

With reference to FIG. 8, the positions of the detector heads 10, 12 are shown for a total Body Planar data acquisition. A patient is diagrammatically indicated in FIG. 8 by ovals representing the head H, torso T, arms A, legs L, and feet F. The patient is laid on the patient support or pallet 18 (diagrammatically indicated in FIG. 8). The two radiation detectors 10, 12 are oriented above and below the patient's body, respectively. The capacitive sensor array of the top detector 10 is used to measure the nearest detector head-to-patient distance (measured distances indicated diagrammatically by arrows in FIG. 8). This measurement is then used as a reference signal to dynamically position the detector vertically so as to achieve a specified gap between the array and the patient. If the pallet 18 is electrically conductive, then the capacitive sensor array of the bottom detector 12 is also optionally used to keep the detector head-to-pallet distance constant as the detector head 12 moves. Alternatively, the bottom detector head 12 may be moved without such feedback control, under the assumption that the pallet 18 has a substantially uniform and straight lower profile.

In the total body planar imaging data acquisition of FIG. 8, the detectors 10, 12 are moved along the patient's body from head to foot (as shown in FIG. 8), or from foot to head. For example, in the head-to-foot image data acquisition of FIG. 8, the illustrated detector positions 10', 12' indicate the positions of the detector heads 10, 12, respectively, at a later time in the head-to-foot acquisition. As such, it is advantageous to have the edge capacitive elements 76 oriented such that they measure distance "ahead" of the detector head 10, so as to sense upcoming outward changes in patient profile feet F shown in FIG. 8. This allows the system additional time to raise the detector 10 so as to avoid contact with the feet 10 while still maintaining the desired detector-to-patient gap as long as possible.

With reference to FIG. 9, in a Cardiac imaging data acquisition, the detectors 10, 12 are oriented at a 90° relative angle with respect to each other. In FIG. 9, a view of the patient looking down on the patient's head is shown, using representative ovals labeled as in FIG. 8 with the addition of a partial oval indicative of the patient's belly B. For the cardiac acquisition, the detector heads 10, 12 should be as close as possible to the patient to optimize image quality. Accordingly, the closest proximity value given by any of the capacitive elements 60 is used as the guiding proximity signal to position the detectors. In the cardiac acquisition, the close proximity of the two detector heads 10, 12 to each other is a complicating factor. Erroneous proximity information could be provided if the closest detected proximity is actually to the other detector head, rather than to the patient. To address this problem, in some embodiments the two detector heads 10, 12 are arranged as master and slave heads, respectively, and are configured to be in synchronization with each other with a raster sequencing on the radiation sensitive-face of one radiation detector head mirrored on the radiation sensitive-face of the other radiation detector head. By performing an offset and gain calibration, as described with reference to FIG. 6, with no objects in between the detectors 10, 12, the influence of each detector head on the other can be canceled out. In the embodiment illustrated in FIG. 9, the raster sequencing start signal is superimposed on a 100 KHz signal 130 sent from the master detector head 10 cover to the slave detector head 12.

In the cardiac acquisition of FIG. 9, or in a tomographic acquisition example (not illustrated) in which the two detector heads positioned on opposite sides of the patient, imaging data of the patient are acquired at a number of azimuth angles, so at each azimuth angle it is advantageous for the proximity sensor system to provide an updated measurement of the detector head-to-patient distance. Since the human body is an irregular shape, with each new azimuth a different one or group of the parallel plate capacitors 60 will typically provide the "nearest" measurement. Accordingly, the "nearest" measurement acquired by raster sampling of all the parallel plate capacitors 60 is suitably used as the minimum detector head-to-patient distance.

With reference to FIGS. 10A, 10B, 10C, and 11, another embodiment is illustrated. FIGS. 10A, 10B, and 10C show respective front, side, and top views of a gamma camera 180 that includes two detector heads 210, 212 mounted on robotic manipulators 220, 222 that in turn are mounted on a circular gantry 224. In the illustrated embodiment, the two detector heads 210, 212 are positioned at 180° azimuthal separation, such as is suitable for a tomographic acquisition, or for a planar acquisition such as that illustrated in FIG. 8. By rotating one detector head and its robotic manipulator azimuthally 90° around the circular gantry 224 (not shown in FIGS. 10A, 10B, and 10C), the detector heads can be set up to perform the cardiac acquisition of FIG. 9. FIG. 11 shows a perspective view of one of the radiation detector heads 210, 212. This detector head includes 54 front proximity sensing capacitive elements 260 arranged in a 6×9 grid distributed over and substantially covering the radiation-sensitive face. The areas of the capacitive elements 260 are varied across the radiation-sensitive face similarly to that shown in FIG. 2. Additionally, four side proximity sensing capacitive elements 276 are shown on the side of the detector head 210, 212. The proximity-sensing capacitive elements 260 are suitably configured similarly to the configuration already described for the proximity-sensing capacitive elements 60, while the proximity-sensing capacitive elements 276 are suitably configured similarly to the configuration already described for the proximity-sensing capacitive elements 76. Thus, the proximity-sensing capacitive elements 260, 276 are suitably used for proximity sensing and collision detection.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A radiation detector head comprising:
   a radiation-sensitive face comprising a radiation-sensitive portion configured to detect radiation; and
   a plurality of capacitive elements disposed over the radiation-sensitive portion and configured to detect a proximity of a subject to the radiation-sensitive face, as well as a collision between the subject and the radiation-sensitive face.

2. The radiation detector head as set forth in claim 1, wherein the radiation-sensitive face includes:
   a radiation collimator; and
   an array of radiation detectors arranged to detect radiation after said radiation passes through the radiation collimator.

3. The radiation detector head as set forth in claim 2, wherein the array of radiation detectors includes one of:
   (i) one or more scintillators optically coupled with a plurality of light sensors arranged to view the one or more scintillators, and
   (ii) a plurality of radiation-sensitive elements configured to absorb radiation and output an electrical signal responsive thereto.

4. The radiation detector head as set forth in claim 1, wherein the radiation-sensitive surface is generally planar, and the plurality of capacitive elements include:
   an array of conductive plates distributed across and aligned parallel with the radiation-sensitive face.

5. The radiation detector head as set forth in claim 4, wherein the radiation-sensitive face includes:
a radiation collimator arranged to collimate radiation along a direction generally transverse to the generally planar radiation-sensitive surface; and
an array of radiation detectors arranged to detect radiation after said radiation passes through the radiation collimator.

6. The radiation detector head as set forth in claim 4, wherein the array of conductive plates are electrically interconnected to support sampling of an electrical characteristic associated with each capacitive plate.

7. The radiation detector head as set forth in claim 6, wherein the sampled electrical characteristic includes a response to an a.c. electrical signal or a.c. electrical signal component applied to the sampled conductive plate.

8. The radiation detector head as set forth in claim 4, wherein the array of conductive plates includes:
a conductive film that is patterned to define the array of conductive plates.

9. The radiation detector head as set forth in claim 4, wherein the plurality of capacitive elements further include:
a second conductive film spaced apart from the conductive film.

10. The radiation detector head as set forth in claim 9, wherein the second conductive film is patterned such that each capacitive element is a parallel plate capacitor having substantially equally sized conductive parallel plates.

11. The radiation detector head as set forth in claim 4, wherein conductive plates of the array of conductive plates located near a center of the radiation sensitive face have areas substantially smaller than the areas of at least some conductive plates located near an edge of the radiation-sensitive face.

12. The radiation detector head as set forth in claim 1, wherein the radiation-sensitive surface is generally planar, and the plurality of capacitive elements extend less than 5 millimeters from the generally planar radiation-sensitive surface.

13. The radiation detector head as set forth in claim 1, further comprising:
one or more capacitive elements disposed on a side of the radiation detector head and configured to detect proximity to the side of the radiation detector head.

14. The radiation detector head as set forth in claim 1, further comprising:
an outer cover disposed over the radiation-sensitive face and over the plurality of capacitive elements disposed over the radiation-sensitive face.

15. A radiation detector head comprising:
a radiation-sensitive face configured to detect radiation;
a plurality of capacitive elements disposed over the radiation-sensitive face and configured to detect proximity of a subject to the radiation-sensitive face;
wherein the radiation-sensitive surface is generally planar, and the plurality of capacitive elements include an array of conductive plates distributed across and aligned parallel with the radiation-sensitive face; and
wherein the array of conductive plates are electrically interconnected to support sampling of an electrical characteristic associated with each capacitive plate; and
wherein the plurality of capacitive elements further comprise spaced apart parallel conductive plates defining a plurality of parallel-plate capacitors distributed across the radiation-sensitive face, and the sampled electrical characteristic includes a conductive electric current flowing between the parallel conductive plates responsive to compressive force against at least one of the parallel conductive plates.

16. The radiation detector head as set forth in claim 15, wherein the sampled electrical characteristic further includes a capacitance, admittance, or impedance of each parallel-plate capacitor.

17. A gamma camera comprising:
a plurality of radiation detector heads, at least one radiation detector head including a plurality of capacitive elements disposed over at least a radiation-sensitive portion of the radiation detector head; and
a proximity sensor monitor coupled with the plurality of capacitive elements to detect proximity of a subject to the radiation detector head based on a measured electrical characteristic of the capacitive elements.

18. The gamma camera as set forth in claim 17, wherein the proximity sensor monitor is configured to successively sample each capacitive element of the plurality of capacitive elements to detect the measured electrical characteristic generated by that capacitive element.

19. The gamma camera as set forth in claim 18, wherein the proximity sensor monitor is further configured to bias capacitive elements neighboring the sampled capacitive element to reduce an effect of the neighboring capacitive elements on the measured electrical characteristic.

20. A gamma camera comprising:
a plurality of radiation detector heads, at least one radiation detector head including a plurality of capacitive elements disposed over at least a radiation-sensitive portion of the radiation detector head; and
a proximity sensor monitor coupled with the plurality of capacitive elements to detect proximity of a subject to the radiation detector head based on a measured electrical characteristic of the capacitive elements;
wherein the plurality of capacitive elements include spaced apart conductive plates, and the proximity sensor monitor is configured to detect a conductive electrical current between the conductive plates produced by compressive reduction or compressive elimination of a gap between the spaced apart conductive plates.

21. A gamma camera comprising:
a movable radiation detector head;
at least one capacitive element disposed on the radiation detector head and including spaced apart parallel conductive plates; and
a collision sensor monitor configured to detect conductive electric current flowing between the parallel conductive plates responsive to mechanical deformation of the spacing between the plates.

* * * * *